(12) United States Patent
Okada et al.

(10) Patent No.: US 8,221,306 B2
(45) Date of Patent: Jul. 17, 2012

(54) ENDOSCOPE THERAPEUTIC DEVICE

(75) Inventors: Yuta Okada, Hachioji (JP); Ryuta Sekine, Koganei (JP); Raifu Matsui, Hino (JP)

(73) Assignee: Olympus Corporation, Tokyo (JP)

( * ) Notice: Subject to any disclaimer, the term of this patent is extended or adjusted under 35 U.S.C. 154(b) by 117 days.

(21) Appl. No.: 12/612,461

(22) Filed: Nov. 4, 2009

(65) Prior Publication Data

US 2010/0048992 A1  Feb. 25, 2010

Related U.S. Application Data

(63) Continuation of application No. 11/104,883, filed on Apr. 13, 2005, now abandoned.

(30) Foreign Application Priority Data

Apr. 13, 2004  (JP) ................................ 2004-118182

(51) Int. Cl.
*A61B 1/00* (2006.01)
(52) U.S. Cl. ........................................ 600/106; 600/129
(58) Field of Classification Search .................. 600/104, 600/106, 114, 129, 137, 127; 356/241.1
See application file for complete search history.

(56) References Cited

U.S. PATENT DOCUMENTS

| | | | |
|---|---|---|---|
| 3,835,854 A * | 9/1974 | Jewett ........................... | 604/159 |
| 4,452,236 A | 6/1984 | Utsugi | |
| 4,674,515 A * | 6/1987 | Andou et al. .................. | 600/463 |
| 4,756,303 A | 7/1988 | Kawashima et al. | |
| 5,060,632 A * | 10/1991 | Hibino et al. .................. | 600/109 |
| 5,100,421 A | 3/1992 | Christoudias | |
| 5,251,356 A * | 10/1993 | Oaki et al. ............... | 15/104.095 |
| 5,318,528 A * | 6/1994 | Heaven et al. .............. | 604/95.01 |
| 5,349,940 A * | 9/1994 | Takahashi et al. ......... | 356/241.4 |
| 5,511,564 A | 4/1996 | Wilk | |
| 5,683,349 A | 11/1997 | Makower et al. | |
| 5,808,665 A * | 9/1998 | Green ............................ | 348/65 |
| 5,817,119 A * | 10/1998 | Klieman et al. ............... | 606/174 |

(Continued)

FOREIGN PATENT DOCUMENTS

EP   1426072 A1   6/2004

(Continued)

OTHER PUBLICATIONS

U.S. Office Action dated Jan. 9, 2008 of related U.S. Appl. No. 11/104,883.

(Continued)

*Primary Examiner* — Anhtuan Nguyen
*Assistant Examiner* — Alireza Nia
(74) *Attorney, Agent, or Firm* — Scully, Scott, Murphy & Presser, P.C.

(57) ABSTRACT

In an endoscope therapeutic device having a plurality of introduction guide tubes for introducing a treatment tool into a body cavity, the introduction guide tubes are mutually joined at a position more proximal than bending portions thereof. Accordingly, the effects caused by the movement of the plurality of the introduction guide tubes are mutually invalidated at a joint portion as a fulcrum, so that the position of the introduction guide tube is relatively stabilized in the body cavity. As joining methods, there are integration, usage of a joint tool, and usage of an over tube. The operability is improved when the introduction guide tube is provided at the distal end thereof with a mechanism for retaining and/or rotating a distal end of a treatment tool inserted therethrough.

6 Claims, 14 Drawing Sheets

U.S. PATENT DOCUMENTS

| | | | |
|---|---|---|---|
| 5,827,175 A * | 10/1998 | Tanaka | 600/104 |
| 6,066,090 A | 5/2000 | Yoon | |
| 6,071,233 A | 6/2000 | Ishikawa et al. | |
| 6,234,958 B1 | 5/2001 | Snoke et al. | |
| 6,331,166 B1 | 12/2001 | Burbank et al. | |
| 6,352,503 B1 | 3/2002 | Matsui et al. | |
| 6,569,085 B2 | 5/2003 | Kortenbach et al. | |
| 6,632,227 B2 | 10/2003 | Adams | |
| 6,726,675 B1 * | 4/2004 | Beyar | 604/510 |
| 7,029,435 B2 | 4/2006 | Nakao | |
| 7,048,717 B1 * | 5/2006 | Frassica | 604/165.04 |
| 7,090,683 B2 * | 8/2006 | Brock et al. | 606/130 |
| 2003/0092966 A1 * | 5/2003 | Schara et al. | 600/173 |
| 2003/0100892 A1 * | 5/2003 | Morley et al. | 606/1 |
| 2003/0176767 A1 | 9/2003 | Long | |
| 2003/0219184 A1 * | 11/2003 | Rio | 384/523 |

FOREIGN PATENT DOCUMENTS

| | | | |
|---|---|---|---|
| JP | 56008028 A | 1/1981 | |
| JP | 2007008450 A | 1/1995 | |
| JP | 10146316 A | 6/1998 | |
| JP | 11192203 A | 7/1999 | |
| JP | 2000-033071 | 2/2000 | |
| JP | 2000037390 A | 2/2000 | |
| JP | 2000166936 A | 6/2000 | |
| JP | 2000325303 A | 11/2000 | |
| JP | 2002538873 | 11/2002 | |
| WO | 0054653 A1 | 9/2000 | |
| WO | 0158360 A2 | 8/2001 | |

OTHER PUBLICATIONS

U.S. Office Action dated Sep. 3, 2008 of related U.S. Appl. No. 11/104,883.
U.S. Office Action dated Jan. 30, 2009 of related U.S. Appl. No. 11/104,883.
U.S. Office Action dated Jun. 10, 2009 of related U.S. Appl. No. 11/104,883.
European Search Report dated Oct. 19, 2005 for European Application No. EP 05 00 7799.9.
European Search Report dated Oct. 1, 2008 for European Application No. EP 08 01 4776.2.
Japanese Office Action dated Jan. 19, 2010 from corresponding Japanese Application No. 2004-118182.
Japanese Office Action dated Apr. 6, 2010 from corresponding Japanese Application No. 2004-118182.

* cited by examiner

ENDOSCOPE THERAPEUTIC DEVICE

CROSS-REFERENCE TO RELATED APPLICATION

This application is a continuation application of U.S. patent application Ser. No. 11/104,883 filed Apr. 13, 2005 which is based upon and claims the benefit of priority from prior Japanese Patent Application No. 2004-118182, filed Apr. 13, 2004, the entire contents of each of which are incorporated herein by reference.

BACKGROUND OF THE INVENTION

1. Field of the Invention

The present invention relates to an endoscope therapeutic device for performing treatment under observation via an endoscope by introducing a treatment tool through an introduction guide tube with a bending function into a body cavity, and an introduction guide tube thereof.

2. Description of the Related Art

An endoscope therapeutic device for performing treatment using a treatment tool under observation via an endoscope by introducing the treatment tool through an introduction guide tube into a body cavity is known in the related art. The introduction guide tube used in the endoscope therapeutic device of this type is referred also as a "channel tube". Recently, as an introduction guide tube of this type, an introduction guide tube with a bending function, in which a bending portion is provided in the vicinity of the distal end of the tube, and the bending portion is capable of being bent by a proximal control section is proposed (See JP-A-2000-33071). This endoscope therapeutic device is configured in such a manner that treatment tools are guided via a plurality of introduction guide tubes with a bending function, respectively, into a body cavity, and the directions of the treatment tools in the body cavity are adjusted by bending the bending portions of the introduction guide tubes.

BRIEF SUMMARY OF THE INVENTION

An endoscope therapeutic device according to the present invention includes a plurality of introduction guide tubes for introducing treatment tools into a body cavity, wherein the plurality of introduction guide tubes are joined to each other at portions proximal to the bending portions thereof. In a case where there are a plurality of bending portions on the introduction guide tube, a joint portion is placed in a more proximal position than the distal-most bending portion.

In this manner, the effects caused by the movement of a plurality of the introduction guide tubes are mutually invalidated at a joint portion as a fulcrum, so that the position of the introduction guide tube is relatively stabilized in the body cavity. Therefore, the operability is improved. Also, since the bending portions are located on the more distal side than the joint portion, good operability can be maintained even when they are joined.

The form of joint may be such that a part of the insertion portion that is located on a more proximal side than the bending portion of the introduction guide tube is integrally joined with other introduction guide tubes. In this case, a stable connection is achieved. It is also possible to join the introduction guide tubes with a joint tool. In this case, since the introduction guide tubes can be replaced, it is applicable to various embodiments. It is also possible to provide a connecting function to an over tube through which the introduction guide tubes are inserted.

When the joint tool is resiliently deformed to tighten the introduction guide tubes to be inserted, a stable joint is achieved.

In addition to the introduction guide tubes, the positions of the endoscope, a suction tube, and the like in the body cavity are also stabilized by being joined as a matter of course. Further, an operating mechanism for operating the distal end of the treatment tool to be inserted therethrough may preferably be provided at the distal end of the introduction guide tube. Since the introduction guide tube is provided with a function to operate the treatment tool in addition to the function to receive the treatment tool inserted therethrough, operability is improved. Since the treating portion and an element moved by operation are located close to each other, a delicate operation can be performed.

The operator can operate the treatment tools inserted through the guide tubes without releasing his/her hand from the guide tube by operating on the proximal side of the guide tube, and hence good operability is achieved. The operation of the treatment tool includes, for example, the fore-and-aft movement or the rotation of the treatment tool.

BRIEF DESCRIPTION OF THE SEVERAL VIEWS OF THE DRAWINGS

These and other features, aspects, and advantages of the apparatus and methods of the present invention will become better understood with regard to the following description, appended claims, and accompanying drawings where:

DETAILED DESCRIPTION OF THE INVENTION

Embodiments of the invention will be described below with reference to the accompanying drawings.

Referring now to FIG. 1 to FIG. 7, an endoscope therapeutic device according to a first embodiment of the present invention will be described. FIG. 1A is a perspective view of an endoscope therapeutic device according to the first embodiment of the present invention. A treatment tool introduction guide tube unit 1 is shown in FIG. 1A. FIG. 1B shows an insertion portion 3 of an endoscope 2. In the endoscope therapeutic device according to the first embodiment, the treatment tool introduction guide tube unit 1 is joined to the insertion portion 3 of the endoscope 2 by the joint tool described above.

Figure 2:
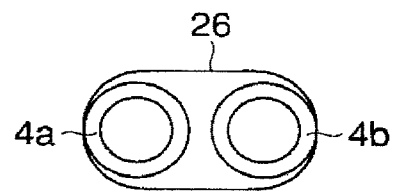
FIG. 2 is a lateral cross-sectional view of a joint portion in the endoscope therapeutic device of FIG. 1A perpendicular to a longitudinal direction of an insertion portion as taken along line 2-2 thereof.

The treatment tool introduction guide tube unit 1 includes a plurality of treatment tool introduction guide tubes 4a, 4b as manipulators for operating the surgical operation tools including the treatment tools such as forceps or the like. The treatment tool introduction guide tubes 4a, 4b are joined at a midsection of an insertion portion 5 thereof by a joint portion 6, and is fixed and joined integrally. A joint hood 26, which constitutes the joint portion 6 is formed of a flexible material. A mode for joining the two treatment tool introduction guide tubes 4a, 4b by the joint hood 26 is shown in FIG. 2. It is also possible to form at least part of the insertion portions 5 of the two treatment tool introduction guide tubes 4a, 4b as a single flexible tube of oval shape in lateral cross-section without using the joint hood 26 as described above. For example, at least the joint portion 6 can be configured in such a manner. In this case as well, a fixed structure in which the insertion portions 5 of a plurality of the treatment tool introduction guide tubes 4a, 4b are connected integrally to each other is provided.

Figure 6:
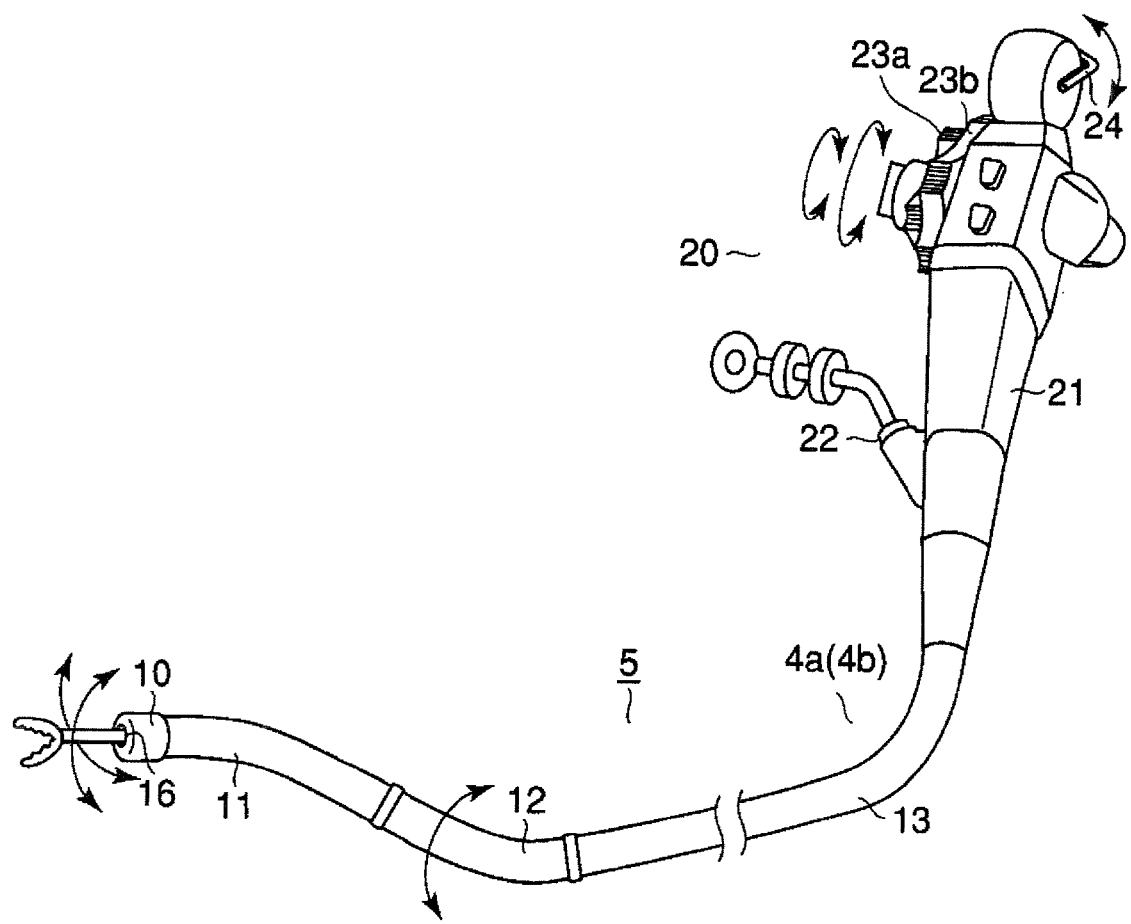
FIG. 6 is a perspective view showing the introduction guide tube in the treatment tool introduction guide tube unit of the endoscope therapeutic device according to the first embodiment.

FIG. 6 is a perspective view of the treatment tool introduction guide tube 4a (4b). As shown in FIG. 6, the insertion portions 5 of the treatment tool introduction guide tubes 4a, 4b each include a distal portion 10 located at a distal end thereof, a first bending portion 11 is located on the proximal side of the distal portion 10, a second bending portion 12 is located on the proximal side of the first bending portion 11, and a flexible portion 13 is provided behind the second bending portion 12. A proximal control section 20 is provided at the proximal end of the insertion portion 5 of each of the treatment tool introduction guide tubes 4a or 4b. The proximal control sections 20 each include a grip portion 21, an insertion port 22 which communicates with a treatment tool guiding channel 14 (see FIG. 7), and a plurality of operating members for bending the bending portions 11, 12 respectively. The operating member for bending includes two angle knobs 23a, 23b for operating the first bending portion 11 in two directions and one angle handle 24 for operating the second bending portion 12 in a single (e.g., vertical) direction.

Figure 7:
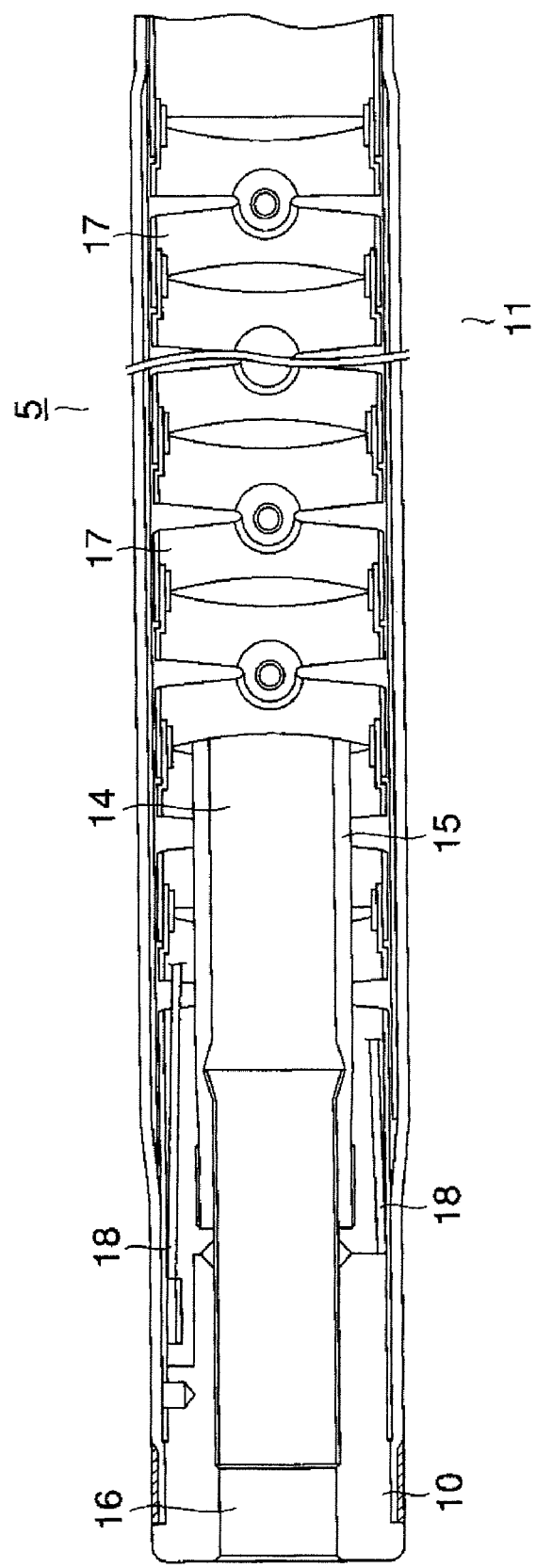
FIG. 7 is a cross-sectional view of a distal end portion of the introduction guide tube in the treatment tool introduction guide tube unit of the endoscope therapeutic device according to the first embodiment.

FIG. 7 is a vertical cross-sectional view of the insertion portion 5 of the treatment tool introduction guide tube in the treatment tool introduction guide tube unit. As shown in FIG. 7, a flexible tube 15 forming the treatment tool guiding channel 14 is disposed over the entire length in the insertion portion 5 of each of the treatment tool introduction guide tubes 4a, 4b. The treatment tool guiding channel 14 opens toward the outside at the distal extremity of the insertion portion 5 via a channel hole 16 at the distal portion 10 and at the control section at the insertion port.

The first bending portion 11 includes a plurality of bending elements 17 joined so as to be capable of rotating freely to allow bending in the vertical and lateral directions, and is bent in the pulling direction of an operating wire 18 by pulling a plurality of the operating wires 18. Although the second bending portion 12 (see FIG. 6) also has the same configuration to be bent by means of a plurality of the bending pieces, the second bending portion 12 is configured so as to be bent only in the vertical direction.

Figures 1A, 1B:
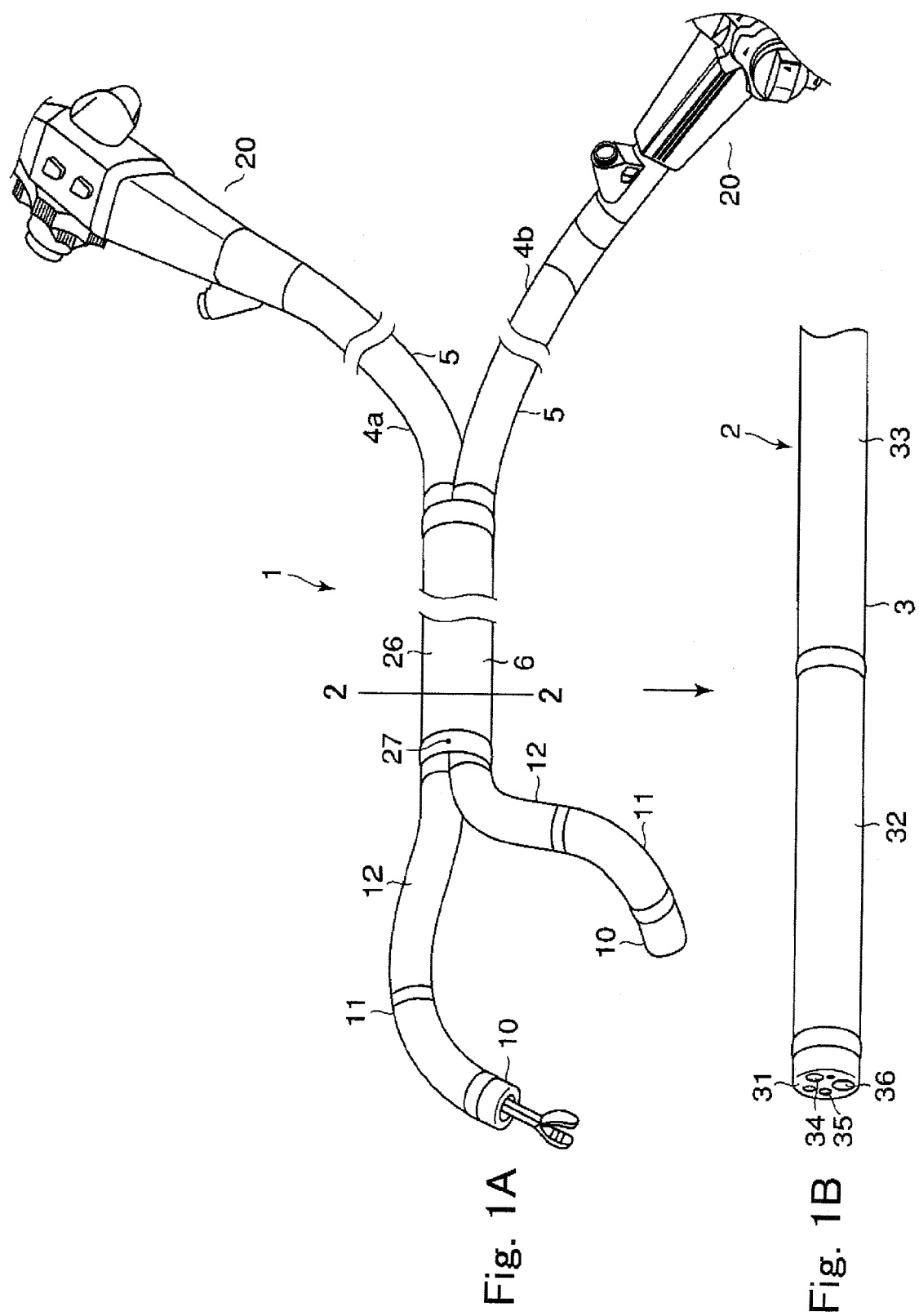
FIG. 1A is a perspective view of an endoscope therapeutic device according to a first embodiment of the present invention.
FIG. 1B is a perspective view of a distal portion of an endoscope for use with the endoscope therapeutic device of FIG. 1A.

As shown in FIG. 1A, the second bending portion 12 is provided so as to extend or project from the distal end of the joint portion 6. In other words, in the respective treatment tool introduction guide tubes 4a, 4b, the proximal portions in the movable sections including the bending portions 11, 12 are fixedly supported by the joint hood 26. In the first embodiment in this configuration, a fixing portion (fixing means) for fixing the portions of the treatment tool introduction guide tubes 4a, 4b in the vicinity of the proximal ends of the bending portions 11, 12 respectively, and then fixing the same to each other is provided. Also, the joint hood 26 constitutes a therapeutic instrument joint tool for joining a plurality of the treatment tool introduction guide tubes 4a, 4b.

Then, the distal end of the joint hood 26 which supports both of the movable sections of the respective treatment tool introduction guide tubes 4a, 4b serves as a common fulcrum 27. Therefore, the movable sections including the bending portions 11, 12 can move respectively on the basis of the common fulcrum 27. The fulcrum 27 is also a common fixed point for the movable sections of the respective treatment tool introduction guide tubes 4a, 4b.

Subsequently, referring to FIG. 1B, the endoscope 2 will be described. FIG. 1B is a perspective view of the insertion portion 3 of the endoscope 2. As shown in FIG. 1B, the insertion portion 3 of the endoscope 2 includes a distal portion 31 located at a distal extremity thereof, a bending portion 32 located on the proximal side of the distal portion 31, and a flexible portion 33 located on the proximal side of the bending portion 32. The endoscope 2 has an observation function by the provision of an inspection window 34, an illumination window 35, and a channel port 36 at the distal end surface of the distal portion 31. The bending portion 32 is bent by a control section (not shown) provided at a proximal end of the insertion portion 3.

Figure 3:
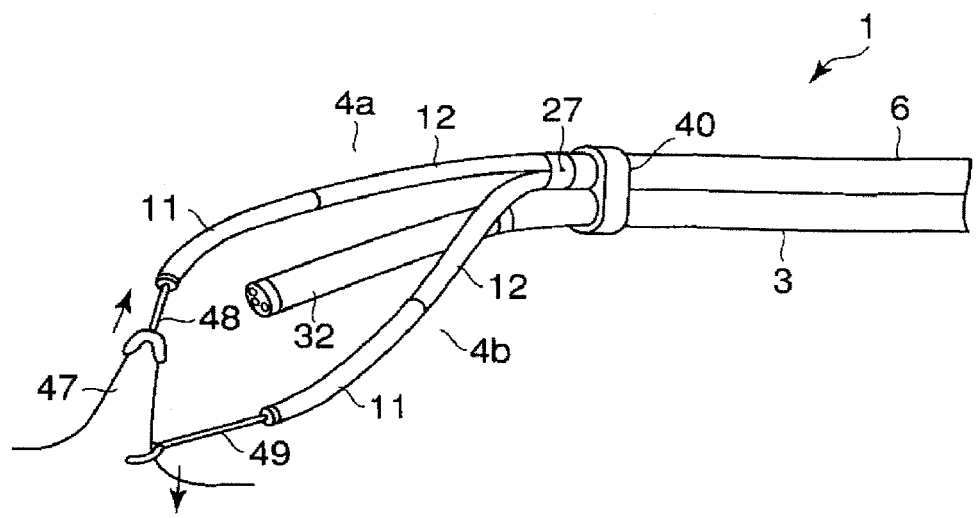
FIG. 3 is an explanatory drawing showing the state of usage of the endoscope therapeutic device according to the first embodiment.

FIG. 3 is an explanatory drawing showing the state of usage of the endoscope therapeutic device 1 including the treatment tool introduction guide tubes 4a, 4b and the endoscope 2 assembled together according to the first embodiment. As shown in FIG. 3, the treatment tool introduction guide tube unit 1 is joined to the insertion portion 3 of the endoscope 2 by a joint tool 40 in a state of being placed along the insertion portion 3 of the endoscope 2. The joint tool 40 is disposed in the vicinity of the distal end of the flexible portion 33 averting the bending portion 32 of the endoscope 2. Since the portion of the treatment tool introduction guide tube unit 1 in the vicinity of the distal end is joined by the joint tool 40, the movable sections of the respective treatment tool introduction guide tubes 4a, 4b including the bending portions 11, 12 are disposed corresponding to the bending portion 32 of the endoscope 2, and are configured to be movable with respect to each other.

Figure 4:
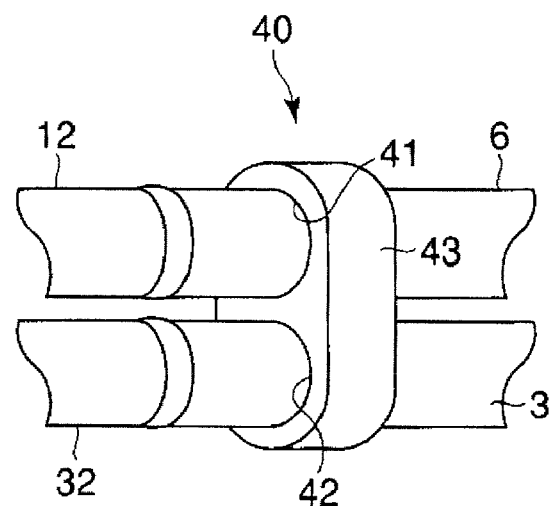
FIG. 4 is a perspective view showing the joint in an enlarged manner in a state in which a treatment tool introduction guide tube unit is attached to the endoscope in the endoscope therapeutic device according to the first embodiment.
Figure 5:
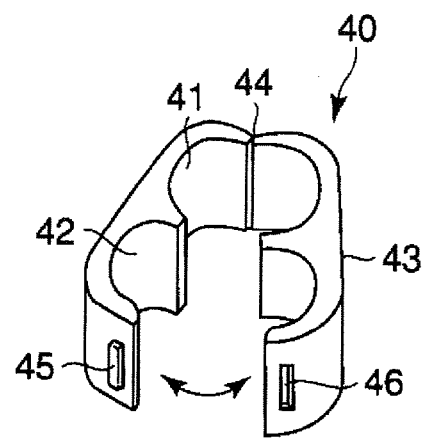
FIG. 5 is a perspective view showing the joint for assembling the treatment tool introduction guide tube unit to the endoscope in the endoscope therapeutic device according to the first embodiment.

As shown in FIG. 4 and FIG. 5, the joint tool 40 includes a band member 43 having an insertion hole 41 for allowing the joint portion 6 of the treatment tool introduction guide tube unit 1 to be inserted therethrough and an insertion hole 42 for allowing the insertion portion 3 of the endoscope 2 to be inserted therethrough, and the band member 43 is capable of opening and closing so that one end can be opened about a hinge 44 on the other end. A projection 45 is formed on one of the edges at the openable end of the band member 43 and a corresponding hole 46 for receiving the projection 45 for engagement is formed on the other edge.

Subsequently, a case of using the endoscope therapeutic device will be described. As shown in FIG. 3, the operator assembles the treatment tool introduction guide tube unit 1 to the insertion portion 3 of the endoscope 2 and guides the same into a body cavity as one unit. When guiding the unit assembled into one piece into the body cavity as described above, it is also possible to guide it into the body cavity using a trocar or an over tube (not shown) as a guiding member as is known in the art.

Then, the operator introduces the various treatment tools (including a suction tool) into the body cavity via the respective treatment tool introduction guide tubes 4a, 4b of the treatment tool introduction guide tube unit 1, which are joined to the insertion portion 3 of the endoscope 2, while observing the body cavity by the endoscope 2 to perform a required treatment. It is also possible to introduce another treatment tool through the channel port 36 and corresponding channel provided on the endoscope 2 to perform a treatment simultaneously.

FIG. 3 shows a state in which tissue 47 is pulled upward. In this example of treatment, the operator pulls up the tissue 47 using grasping forceps 48 introduced through one of the treatment tool introduction guide tubes 4a, holds the tissue 47 using the grasping forceps 49 introduced through the other introduction guide tube 4b, and moves the respective treatment tools in the opposite direction. In other words, the operator bends the bending portions 11, 12 of the treatment tool introduction guide tubes 4a, 4b respectively, and provides the opposite movements to the two pairs of forceps 48, 49 to pull the tissue 47.

Here, since the movable sections of the respective treatment tool introduction guide tubes 4a, 4b which guide the respective grasping forceps 48, 49 move in the opposite directions with reference to the fulcrum 27, supporting forces exerted to the fulcrum 27 are mutually invalidated (canceled), and the movable sections of the respective treatment tool introduction guide tubes 4a, 4b move with reference to the fulcrum 27. The fulcrum 27 is approximately considered as a fixed point. Therefore, a force to be exerted to the grasping forceps 48, 49 does deviate and can be exerted to the tissue 47 as is. Such behavior is not limited to the case of puling up the tissue 47, but may be the same in the surgical operation such as to expand the tissue 47.

In general, in case of using the single introduction guide tube or the flexible endoscope independently, the flexible portion of the insertion portion is suspended in a space of the body cavity by the reaction received from the grasping forceps so as to be capable of moving freely. Therefore, a force exerted to the tissue can become extremely small because the force generated by the reaction is absorbed in the flexible insertion portion.

However, in the first embodiment, since the movable sections of the respective treatment tool introduction guide tubes 4a, 4b which guide the grasping forceps 48, 49 is fixedly supported by the common fulcrum 27, the supporting forces generated by the reaction and exerted to the fulcrum 27 are mutually invalidated at the fulcrum 27, whereby relatively stable support of the movable sections of the treatment tool introduction guide tubes 4a, 4b is achieved. In other words, there is less possibility that the treatment tool introduction guide tubes 4a, 4b move by themselves and hence the force is dissipated. The fulcrum 27 can be regarded as a fixed point, and hence the grip forceps 48, 49 can be guided as intended with reference to the fulcrum 27 to perform a quick operation of treatment. In this manner, even when the two portions of the tissue are gripped by the two treatment tools and the two portions are moved in the opposite directions as in the case of pulling up of the tissue or expanding the tissue, treatment can be performed with a strong force without any undesirable movement of the treatment tool introduction guide tubes 4a, 4b and/or the endoscope 2.

In the first embodiment described above, the case in which the treatment tool introduction guide tube unit 1 is used by being joined to the insertion portion 3 of the endoscope 2 has been described. However, the same advantages can be achieved in the case in which the treatment tool introduction guide tube unit 1 having a plurality of the treatment tool introduction guide tubes joined to each other is used independently. However, when the treatment tool introduction guide tube unit 1 is used by being joined to the insertion portion 3 of the endoscope 2, the positional relation with respect to the endoscope 2 is established during use, and hence the surgical situation can be observed easily, and the stable supporting balance is provided to the entire unit, whereby stability of operation is increased, thereby improving usability.

In the case in which the treatment tool is used via the channel provided in the endoscope 2, the form of usage in which the supporting function is provided as described above is also conceivable as well as other various forms of usage.

Referring now to FIG. 8 to FIG. 11, the endoscope therapeutic device according to a second embodiment of the present invention will be described. The same parts to those in the embodiment described above will be represented by the same reference numerals in the description.

Figure 8:
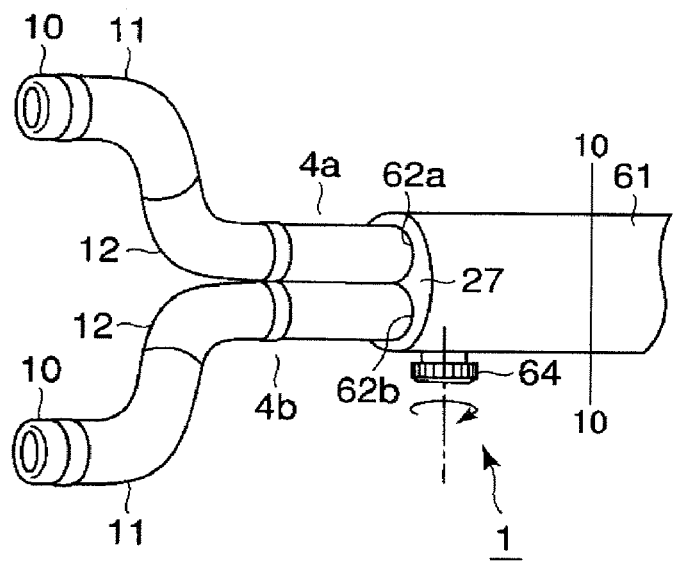
FIG. 8 is a partial perspective view of the endoscope therapeutic device according to a second embodiment of the present invention.

FIG. 8 is a partial perspective view of the endoscope therapeutic device according to the second embodiment of the present invention. As shown in FIG. 8, the treatment tool introduction guide tube unit 1 according to the second embodiment is an assembly of the two treatment tool introduction guide tubes 4a, 4b integrally inserted through an over tube 61 formed of flexible material. The treatment tool introduction guide tubes 4a, 4b are the same as those in the first embodiment.

Figure 9:
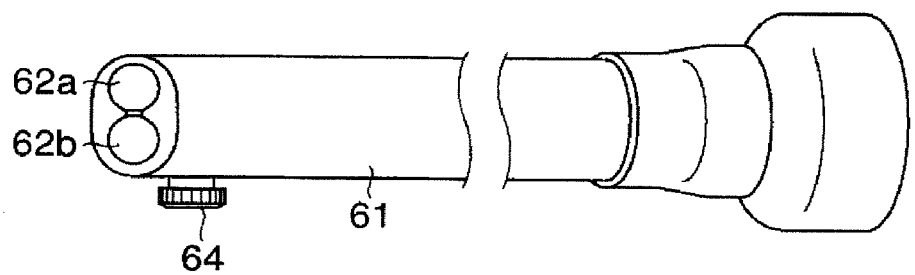
FIG. 9 is a perspective view showing an over tube of the endoscope therapeutic device according to the second embodiment.
Figure 10:
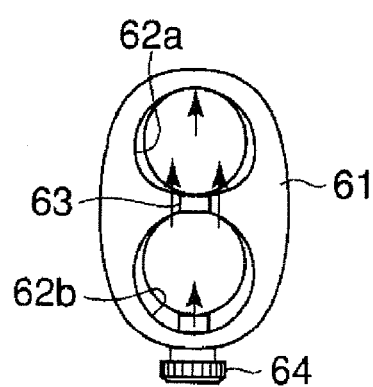
FIG. 10 is a cross-sectional view of a fixed portion of the endoscope therapeutic device of FIG. 8 as taken along line 10-10 thereof.

FIG. 9 is a perspective view showing the over tube 61 of the endoscope therapeutic device according to the second embodiment, and FIG. 10 is a lateral cross-sectional view of a fixed portion of the treatment tool introduction guide tube built in the over tube 61. As shown in FIG. 9, the over tube 61 is formed with two insertion holes 62a, 62b for inserting the respective two treatment tool introduction guide tubes 4a, 4b separately in a juxtaposed manner. As shown in FIG. 10, although the respective insertion holes 62a, 62b are partitioned by a partitioning wall 63 for guiding the treatment tool introduction guide tubes 4a, 4b separately, the insertion holes 62a, 62b partly communicate with each other and are formed close to each other.

A fixing screw 64 is screwed into a sidewall of one of the insertion holes 62b, and the treatment tool introduction guide tube 4b inserted through the insertion hole 62b is tightened by the screw 64, so that the treatment tool introduction guide tube 4b can be fixed. The treatment tool introduction guide tube 4a inserted through the other insertion hole 62a is tightened by resilient deformation of the over tube 61, which occurs when the treatment tool introduction guide tube 4b is tightened by the screw 64, and is fixed to the insertion hole 62b thereby.

In other words, in the second embodiment in this configuration, the fixing portion (fixing means) for fixing the portions of the treatment tool introduction guide tubes 4a, 4b in the vicinity of the proximal ends of the bending portions 11, 12 respectively and then fixing the same to each other is provided. Also, the over tube 61 itself constitutes the treatment equipment joint tool for joining a plurality of the treatment tool introduction guide tubes 4a, 4b.

As shown in FIG. 8, when the two treatment tool introduction guide tubes 4a, 4b respectively are mounted to the over tube 61, the distal portion 10 and the sections of the bending portions 11, 12 are exposed from the distal end of the over tube 61 and project forward (distally). Normally, the distal ends of the flexible portions 13 are also projected at least slightly when mounted.

Figure 11:
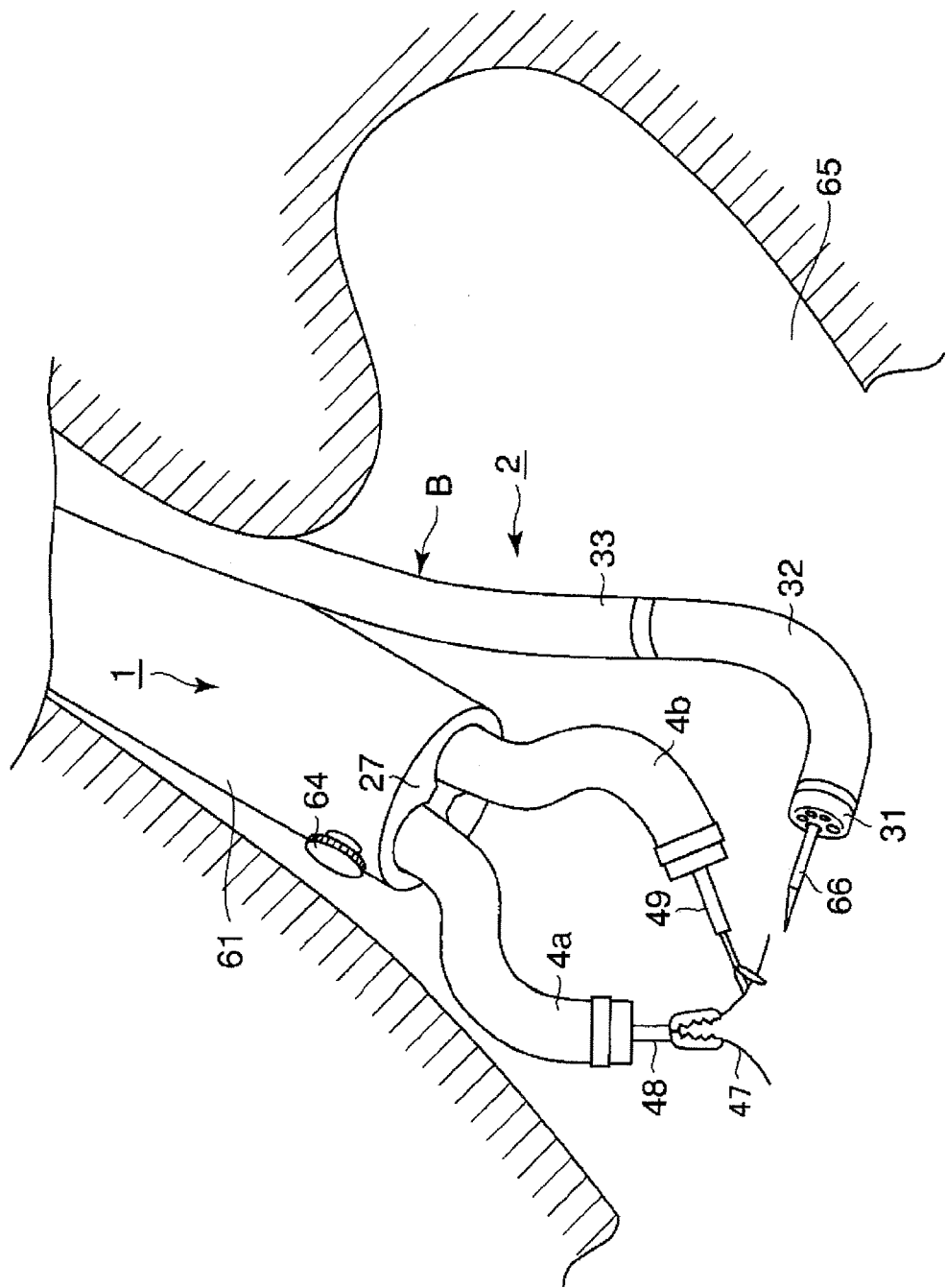
FIG. 11 is an explanatory drawing showing the state of usage of the endoscope therapeutic device according to the second embodiment.

Subsequently, the case where this endoscope therapeutic device is used will be described. FIG. 11 is an explanatory drawing showing the state of usage of the endoscope therapeutic device. As shown in FIG. 11, the operator mounts the two treatment tool introduction guide tubes 4a, 4b to the over tube 61 respectively to form a single unit, and guides the same into the body cavity using the guide means such as trocar. Here, since the treatment tool introduction guide tubes 4a, 4b projecting from the distal end of the over tube 61 are retained with the distal end of the over tube 61 as the fulcrum 27, the movement of the treatment tool introduction guide tubes 4a, 4b is stable and smooth. In a case where the grasping forceps 48, 49 as the treatment tools are operated in the opposite directions by the treatment tool introduction guide tubes 4a, 4b, the components of the force in the opposite directions exerted to the fulcrum 27 are mutually invalidated. Therefore, the movable operating sections of the treatment tool introduction guide tubes 4a, 4b move with reference to the fulcrum 27, and hence the force exerted to the grasping forceps 48, 49 can be exerted to the tissue 47 without dissipation.

Alternatively, the operator can fix the portion in the vicinity of the boundary between the first bending portion 11 and the second bending portion 12 onto the over tube 61 by means of the screw 64 or the like with the sections of the second bending portions 12 of the respective treatment tool introduction guide tubes 4a, 4b positioned within the over tube 61 and with only the first bending portion 11 projected from the over tube 61. In this case, only the first bending portion 11 is bent about the portion in the vicinity of the boundary between the first bending portion 11 and the second bending portion 12 is set as a fulcrum. In other words, the present invention is not limited to the portion in the vicinity of the proximal end of the proximal-most second bending portion 12, but may take a form in which the portion located at the midsection of the bending portion is fixed.

In the second embodiment, the endoscope 2 is provided separately from the unit, and as shown in FIG. 11, the endoscope 2 can be guided in the body cavity 65 along the over tube 61 of the unit for observing the state of treatment, or can guide a treatment tool such as a separate electrosurgical knife 66. FIG. 11 shows a state of incising the tissue 47, which is pulled up by the grasping forceps 48, 49, by means of the electrosurgical knife 66 introduced through the endoscope 2.

Figure 12:
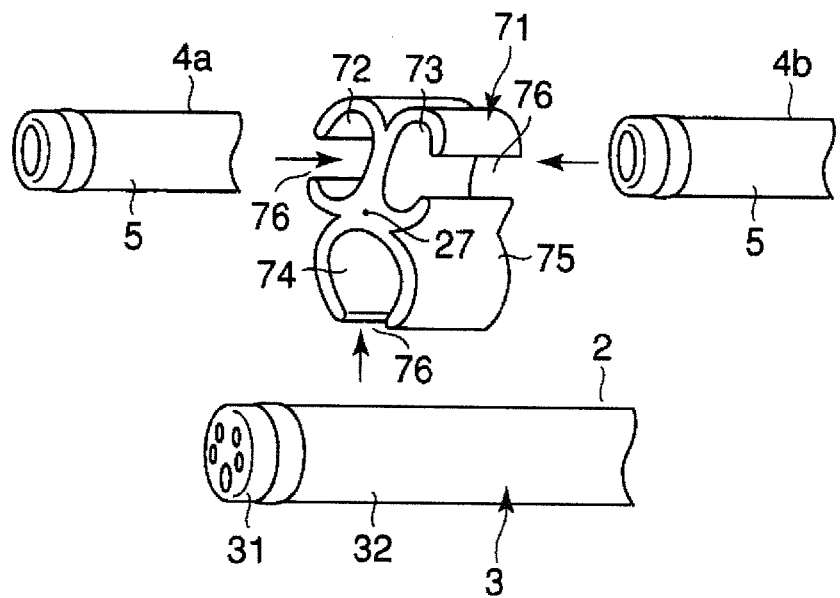
FIG. 12 is an explanatory drawing showing the joint method realized by a joint tool according to a third embodiment of the present invention.
Figure 13:
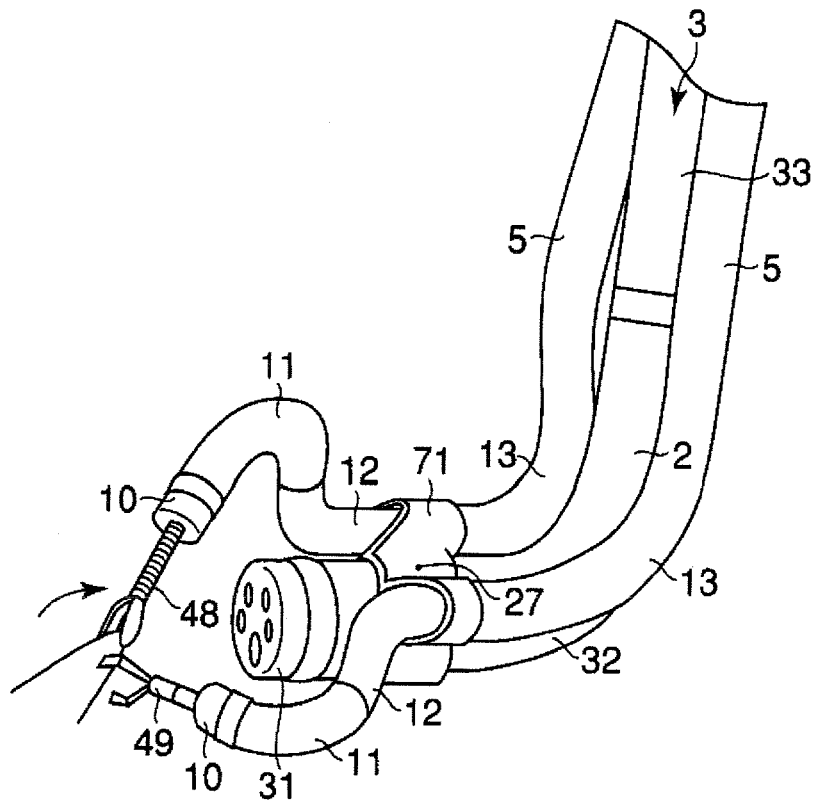
FIG. 13 is an explanatory drawing showing the state of usage of the endoscope therapeutic device according to the third embodiment.

Referring now to FIG. 12 and FIG. 13, the endoscope therapeutic device according to a third embodiment of the present invention will be described. The same parts as in the embodiments described above are represented by the same reference numerals.

The third embodiment is configured in such a manner that the above-described two treatment tool introduction guide tubes 4a, 4b and the endoscope 2 are joined by a joint tool 71. As shown in FIG. 12, the joint tool 71 includes a resilient member 75 having a hole portion 72 for fitting the insertion portion 5 of the treatment tool introduction guide tube 4a, a hole portion 73 for fitting the insertion portion 5 of the treatment tool introduction guide tube 4b, and a hole portion 74 for fitting the insertion portion 3 of the endoscope 2 disposed radially. The hole portions 72, 73, 74 of the joint tool 71 each are formed with a slit 76 for allowing the member to be put in or removed at the midsection thereof by deforming the portions of the resilient member 75 proximate to the slits 76 to insert the respective insertion portions of the treatment tool introduction guide tubes 4a, 4b and endoscope 2.

FIG. 13 shows the state of usage of the third embodiment. The insertion portion 5 of the treatment tool introduction guide tube 4a, the insertion portion 5 of the treatment tool introduction guide tube 4b, and the insertion portion 3 of the endoscope 2 are mounted by being fitted to the hole portions 72, 73, 74 of the joint tool 71 corresponding thereto, respectively. The joint tool 71 is mounted and fixed to the distal portion 31 of the endoscope 2. In order to fixedly retain the flexible portions 13 of the treatment tool introduction guide tubes 4a, 4b in the vicinity of the distal ends in this position, the supporting portion serves as the fulcrum 27 of the treatment tool introduction guide tubes 4a, 4b. Therefore, as shown in FIG. 13, when the treatment tool introduction guide tubes 4a, 4b and the endoscope 2 are connected by the joint tool 71, the treatment tool introduction guide tubes 4a, 4b are disposed at the position surrounding, and in the vicinity of, the insertion portion 3 of the endoscope 2. Consequently, the same usage as the second embodiment described above is enabled. The joint tool 71 may also be disposed at other positions of the endoscope 2 and/or treatment tool introduction guide tubes 4a, 4b.

Subsequently, referring to FIG. 14, the endoscope therapeutic device according to a fourth embodiment of the present invention will be described. The same parts as in the embodiments described above are represented by the same reference numerals in the description.

An over tube 80 having a bending function is employed in the fourth embodiment. The distal portion of the over tube 80 includes a bending portion 81, and the bending portion 81 is bent by the control section (not shown) disposed on a proximal side of the over tube 80. The over tube 80 is formed with a hole 83 for receiving an introduction guide tube 82 inserted therethrough, two holes 85 for receiving two respective suction tubes 84a, 84b separately and a hole 86 for receiving the insertion portion 3 of the endoscope 2 in a sectional manner.

Then, when the introduction guide tube 82, the suction tubes 84a, 84b, and the insertion portion 3 of the endoscope 2 are inserted through the corresponding holes 83, 85, 86 of the over tube 80 respectively, these members are unitized. The over tube 80 includes a fixed portion in the vicinity of the distal portion thereof, so that the inserted tools can be supported so that the relative position between the over tube 80 and the inserted tools does not change in the radial direction. The introduction guide tube 82 and the suction tubes 84a, 84b are mounted to the over tube 80 so as to be capable of moving in the fore-and-aft direction without wobbling in the radial direction. The movable sections of the introduction guide tube 82 and the suction tubes 84a, 84b projecting from the distal end of the over tube 80 are formed with bending portions 87 which are similar to that described above with regard to the treatment tool introduction guide tubes 4a, 4b. The proximal portions of the bending portions 87 projecting from the distal end of the over tube 80 are supported by the over tube 80, and the portions of the over tube 80 in the vicinity of the distal end serves as a fulcrum of the movable sections projecting forward therefrom.

Figure 14:
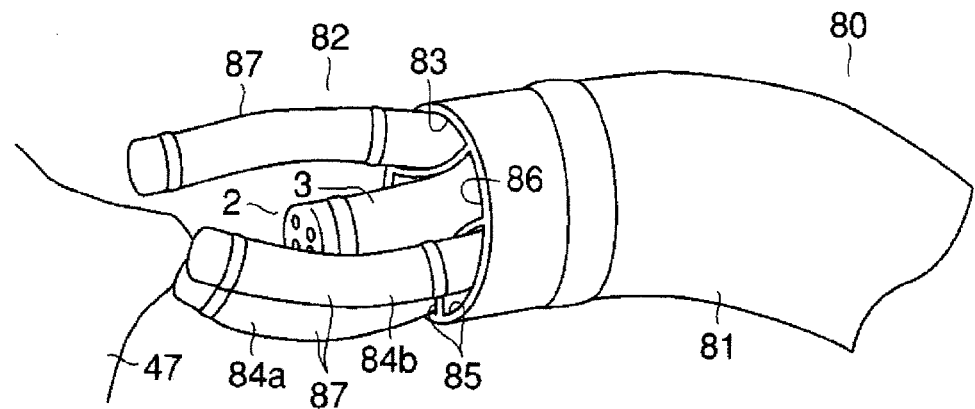
FIG. 14 is a perspective view showing a distal end of the endoscope therapeutic device according to a fourth embodiment of the present invention.

When using this unit, as shown in FIG. 14, the operator causes the introduction guide tube 82, the suction tubes 84a, 84b, and the insertion portion 3 of the endoscope 2 to project from the distal end of the over tube 80. Then, for example, the distal ends of the two suction tubes 84a, 84b are placed on the tissue 47 to adsorb the tissue 47. The operator can also bend the bending portion 87 of the suction tubes 84a, 84b which are projected from the distal end of the over tubes 80 as needed and pull the tissue 47 upward. The operator can also expand the tissue 47 by bending the bending portions 87 of the suction tubes 84a, 84b, which are projected from the distal end of the over tube 80, as needed in the directions away from each other.

In the usage thereof, since the movable sections of the respective suction tubes 84a, 84b are fixedly supported at the common fulcrum, the reaction forces exerted to the suction tubes 84a, 84b are mutually invalidated, so that the suction tubes 84a, 84b can be operated reliably with a strong force as intended about the distal end of the over tube 80 as the fulcrum. The treatment tools may be projected from the introduction guide tube 82 for treatment.

The introduction guide tube 82 may be used as the suction tube. Alternatively, the suction tubes 84a, 84b may be replaced by the treatment tool introduction guide tubes, which are similar to that described above.

Figure 15:
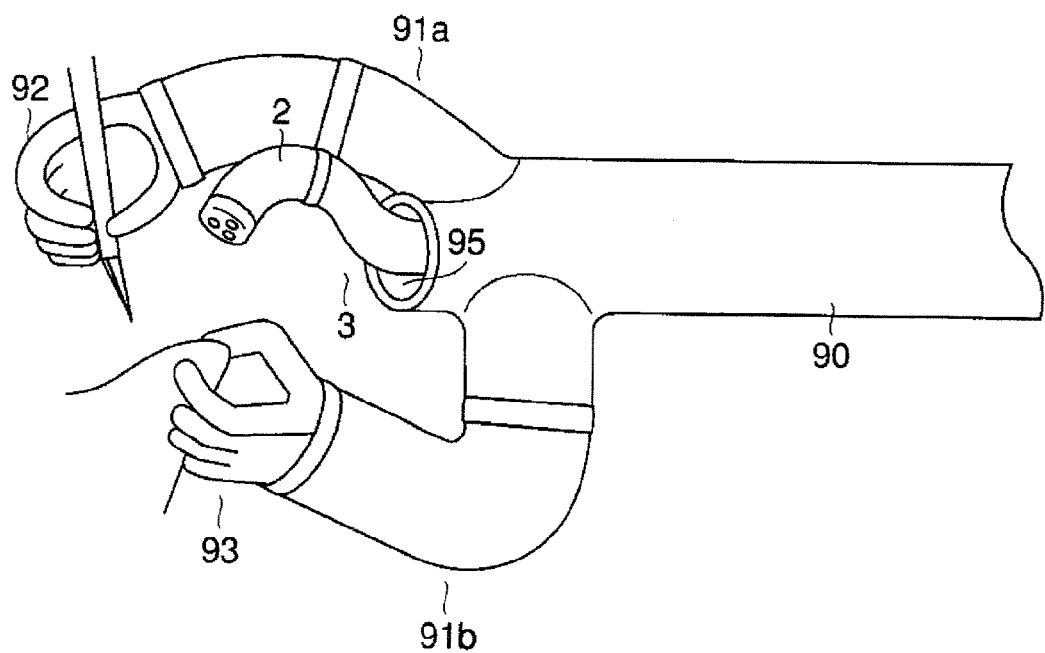
FIG. 15 is a perspective view showing the distal end of the endoscope therapeutic device according to a fifth embodiment of the present invention.

Referring now to FIG. 15, the endoscope therapeutic device according to a fifth embodiment of the present invention will be described. The same parts as in the embodiments described above are represented by the same reference numerals for description.

In the fifth embodiment, an over tube 90 is employed. The over tube 90 is formed integrally with a plurality of manipulators 91a, 91b at the distal end of the over tube 90. One of the manipulators 91a is provided with a distal operating section 92 having flexibility, which is similar to the movement of the fingers of a human being, and the other manipulator 91b is provided with a bending portion 93 with the bending function having flexibility which is similar to the movement of the wrist or elbow of a human being. The respective manipulators 91a, 91b are separately and remotely operated by an operation input means (not shown). The operation input means may be, for example, a glove-type input device to which the movement of the hand of the human being is input and mimicked by the manipulators 91a, 91b.

The over tube 90 is formed with an insertion channel 95 to which the insertion portion 3 of the endoscope 2 is introduced. The endoscope 2 used here has an extra thin insertion portion 3 having only an observing function.

When using the endoscope therapeutic device, as shown in FIG. 15, the operator performs treatment by gripping the treatment tool or by nipping the tissue directly using the left and right manipulators 91a, 91b which have flexibility similar to the movement of the fingers of the human being. In this treatment form, since the movement similar to the wrist of the human being is achieved and hence it can be used with the similar feelings as a human hand, the operability can further be improved, and the usage can be acquired easily.

The left and right manipulators 91a, 91b are mounted to the distal end of the over tube 90, and fixedly and integrally supported. Accordingly, this supporting portion serves as the fulcrum of the manipulators 91a, 91b as the movable sections. Therefore, in the case of operating in the opposite directions using the respective manipulators 91a, 91b, the forces exerted to the respective manipulators 91a, 91b are mutually invalidated so that the respective manipulators 91a, 91b can be operated reliably with a strong force as intended about the distal end of the over tube 90 as the fulcrum.

Figure 16:
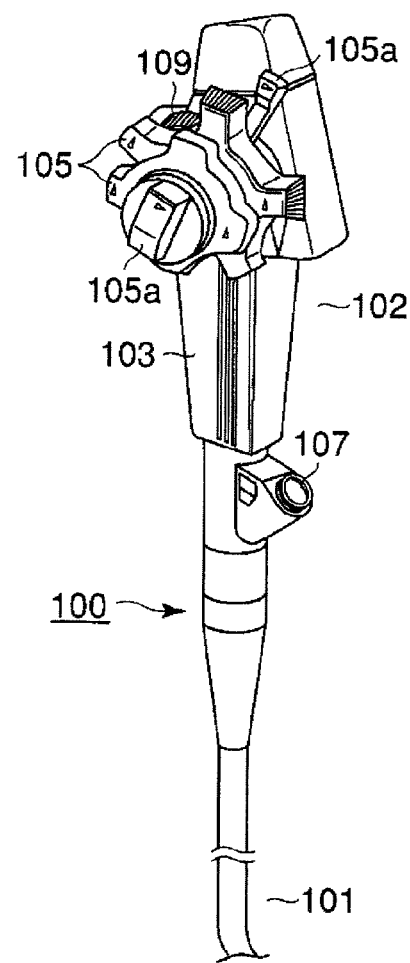
FIG. 16 is a perspective view showing a control section of the introduction guide tube in the endoscope therapeutic device according to a sixth embodiment of the present invention.
Figure 17:
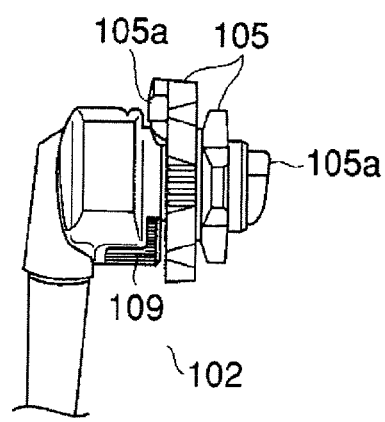
FIG. 17 is a plan view of the control section of the introduction guide tube in the endoscope therapeutic device according to the sixth embodiment.

Referring now to FIG. 16 to FIG. 18, another therapeutic device in which the introduction guide tube as described above is modified will be described as a sixth embodiment of the present invention. As shown in FIG. 16 and FIG. 17, an introduction guide tube 100 in this therapeutic device includes a flexible insertion portion 101 and a control section 102, and the control section 102 includes a grip portion 103, a plurality of angle knobs 105 for bending the bending portion of the insertion portion 101, an insertion port 107 that communicates with a channel of the insertion portion 101, and a treatment tool operating lever 109 for operating a treatment tool operating mechanism, described later. The angle knob 105 is provided with a brake knob 105a for locking the operating position thereof. The brake knob may be provided also on the treatment tool operating lever 109.

Figure 18A:
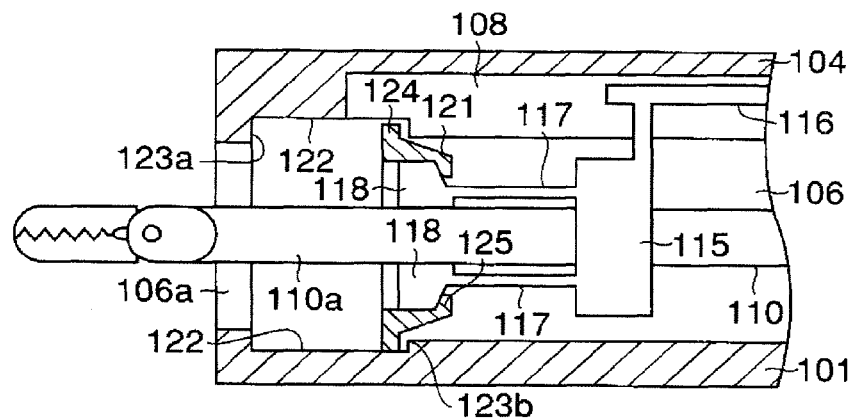
FIG. 18A and FIG. 18B are vertical cross-sectional views of the distal end of the introduction guide tube in the endoscope therapeutic apparatus according to the sixth embodiment.
Figure 18B:
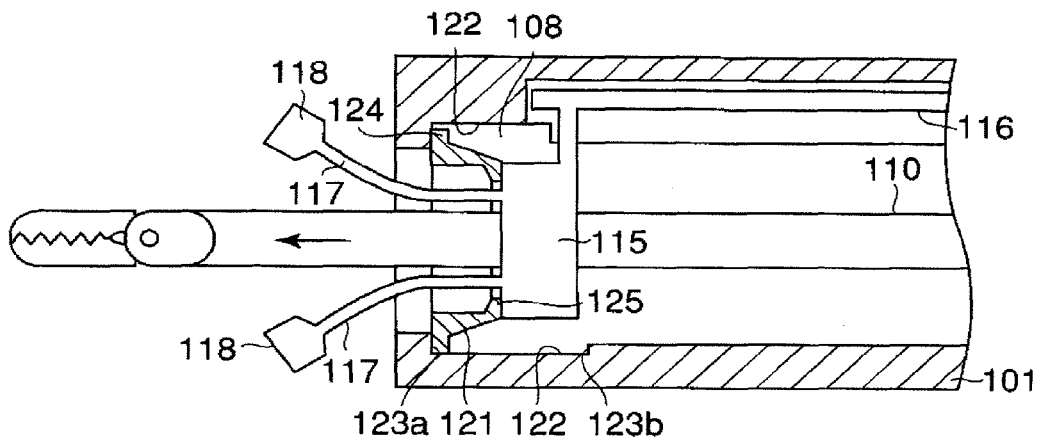

FIG. 18A and FIG. 18B are vertical cross-sectional views of a distal end of the introduction guide tube in the endoscope therapeutic device according to the sixth embodiment. As shown in FIG. 18A and FIG. 18B, an insertion portion 110a of a treatment tool 110, such as grasping forceps, is inserted from the insertion port 107 of the control section 102 of the introduction guide tube 100 through a channel 106, so as to be projected into the body cavity from an opening 106a at the distal end of the channel 106.

A treatment tool operating mechanism 108 is built in the distal portion of the insertion portion 101. The treatment tool operating mechanism 108 here includes a ring-shaped movable element 115 which allows insertion of the insertion portion 110a of the treatment tool 110 in the distal portion of the insertion portion 101 so as to be capable of linear movement in the fore-and-aft axial direction. The distal end of an operating wire 116 inserted through the insertion portion 110 is connected to the movable element 115. Accordingly, a movement control mechanism in which the operating wire 116 is moved in the fore-and-aft axial direction when the treatment tool operating lever 109 of the above-described control section 102 is operated, whereby the movable element 115 of the treatment tool operating mechanism 108 is moved in the fore-and-aft direction and the distal end 110a of the treatment tool 110 is moved in the fore-and-aft direction, is configured. The movable element 115 constitutes a mechanism for selectively engaging and disengaging grip arms 117 as engaging members that engage part of the insertion portion 110a of the treatment tool 110 by the operating wire 116, which is operated on the proximal side.

As shown in FIG. 18A and FIG. 18B, a plurality of the grip arms 117 as engaging members that engage part of the insertion portion 110a of the treatment tool 110 project forward from the movable element 115. The distal portions of the respective grip arms 117 are resiliently biased so as to open outwardly in the free state shown in FIG. 18B. Each grip arm 117 is integrally formed with a holding portion 118 at the distal end thereof. A tightening member 121 is attached on the outside of each grip arm 117, and the tightening member 121 is capable of sliding freely in the range between the movable element 115 and the holding portion 118. The insertion portion 101 is formed with a guide rail 122 in the distal portion so as to guide the tightening member 121 linearly in the fore-and-aft direction. Positioning stoppers (stepped portions) 123a, 123b formed of walls extending vertically upward are formed at the front end and the rear end of the guide rail 122, so that front and rear terminal positions of movement of the tightening member 121 are defined respectively.

The tightening member 121 includes a sliding portion 124 to be guided by the guide rail 122 and a fastening ring portion 125 that slides on the outer periphery of the grip arm 117. As shown in FIG. 18A, when the tightening member 121 is retracted, the respective grip arms 117 are tightened by the tightening member 121, and the holding portions 118 of the respective grip arms 117 are pressed against the outer periphery of the insertion portion 110a of the treatment member 110 to grip the treatment tool 110 by the movable element 115.

By moving the movable element 115 by the operating wire 116 in the fore-and-aft direction in the state in which the treatment tool is constrained as shown in FIG. 18A, the treatment tool 110 can be moved in the fore-and-aft direction together with the movable element 115. In this manner, complicated operation such as to operate with the hand unlinked from the control section of the introduction guide tube 100 or the endoscope as in a case where the operator grips the distal end of the treatment tool 110 directly and pulls and pushes the proximal end of the treatment tool 110 by hand to move the distal portion in the fore-and-aft direction is not necessary, and the fore-and-aft movement of the treatment tool 110 can be performed easily without releasing the hand from the control section.

When the tightening member 121 is moved forward as shown in FIG. 18B, the distal portions of the respective grip arms 117 open and release the treatment tool 110. In other words, the holding portions 118 of the respective grip arms 117 retract from the insertion portion 110a of the treatment tool 110 and release the treatment tool 110 from the gripped state shown in FIG. 18A. Therefore, the treatment tool 110 can be moved in the fore-and-aft direction or in the rotational direction independently of the introduction guide tube 100, whereby the operability of the treatment tool 110 is improved.

The introduction guide tube 100 is used as the introduction guide tube in the device in the therapeutic system described above, and can be used for introduction of various treatment tools. It can also be applied to an unit form in which a plurality of the introduction guide tubes 100 are joined so that the supporting forces exerted to the movable sections of a plurality of the introduction guide tubes 100 are mutually invalidated at the common fulcrum. The general existing introduction guide tube is simply used for inserting the treatment tool therethrough. However, with the introduction guide tube 100 disclosed here, the treatment tool 110 can be rotated or moved in the fore-and-aft direction positively, and hence the reliable operation of the treatment tool 110 is achieved. The introduction guide tube 100 guarantees beneficial effects also when using the introduction guide tube 100 independently and separately from the endoscope 2.

Subsequently, referring to FIG. 19A and FIG. 19B, a modification of the above-described introduction guide tube will be described as a seventh embodiment of the present invention. An introduction guide tube 130 of this type differs from the above-described introduction guide tube 100 in that there is provided a treatment tool advancing-retracting mechanism. In other words, the treatment tool advancing-retracting mechanism supports a separate extremity member 132 at the distal portion 131 of the introduction guide tube 130 via a plurality of push rods 133 so as to be capable of moving in the fore-and-aft direction. The push rods 133 are moved in the fore-and-aft direction by operating the treatment tool operating lever 109 provided on the control section 102 of the introduction guide tube 130, so that the extremity member 132 is moved in the fore-and-aft direction.

Figure 19A:
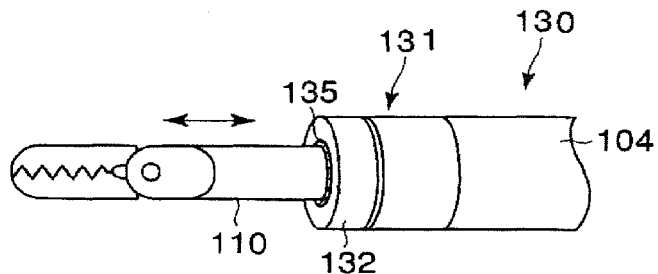
FIG. 19A and FIG. 19B are perspective views showing the distal end of the introduction guide tube in the endoscope therapeutic device according to a seventh embodiment of the present invention.
Figure 19B:
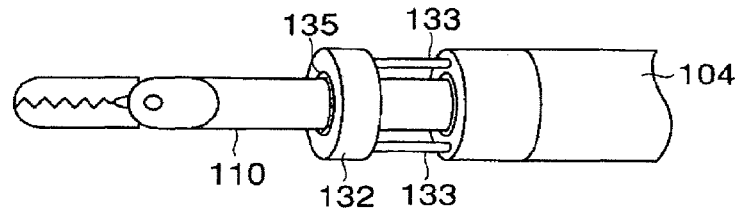

FIG. 19A shows a state in which the extremity member 132 is waiting at a normal position which is retracted backward, and FIG. 19B shows a state in which the extremity member 132 is moved forward.

As shown in FIG. 19A and FIG. 19B, a ring-shaped resilient member 135 as the resilient member is disposed at the peripheral edge of the distal end opening of the channel formed on the extremity member 132. The ring-shaped resilient member 135 is used for gripping the insertion portion of the treatment tool 110 projected from the distal end opening of the channel by tightening the same with a resilient force. The treatment tool 110 is retained by the resiliently tightening force of the ring-shaped resilient member 135 and hence follows the movement of the extremity member 132. However, the force that retains treatment tool 110 is such that when the insertion portion 110a of the treatment tool 110 is pushed and pulled from the proximal side, only the treatment tool 110 can move against the retaining force of the ring-shaped resilient member 135. It is also possible to retain the treatment tool 110 with a force of a strength that cannot move the treatment tool 110.

The above-described introduction guide tube 130 can also be used as the above-described introduction guide tube and as a member for introducing the treatment tool as a matter of course, and it can also be applied to a unit form in which a plurality of the introduction guide tubes 130 are joined so that the supporting forces exerted to the movable sections of a plurality of the introduction guide tubes 130 are mutually invalidated at the common fulcrum.

Figure 20:
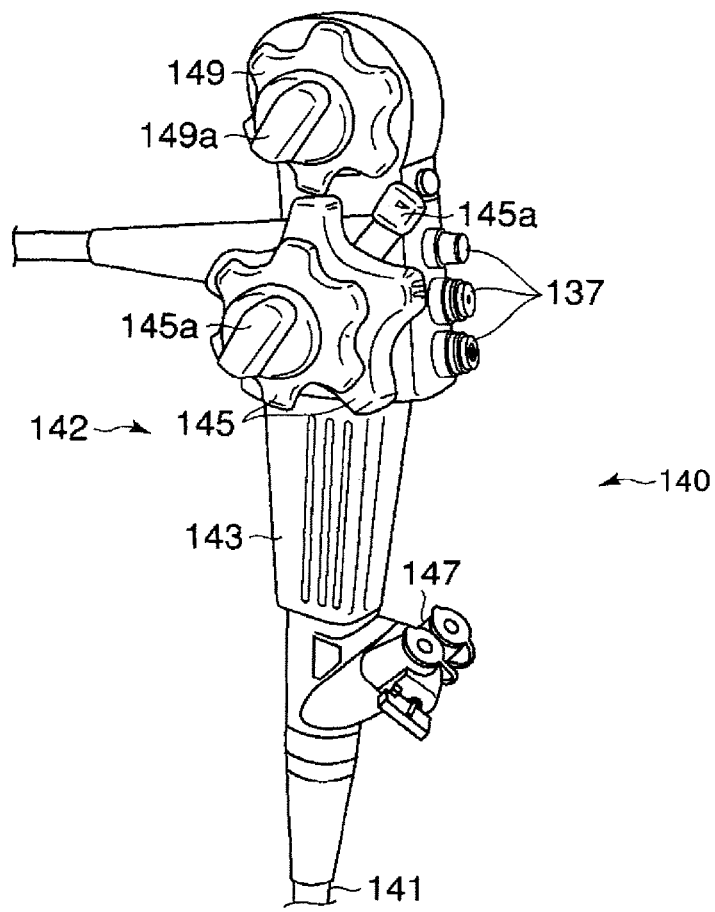
FIG. 20 is a perspective view showing the control section of the introduction guide tube in the endoscope therapeutic device according to an eighth embodiment of the present invention.
Figure 21:
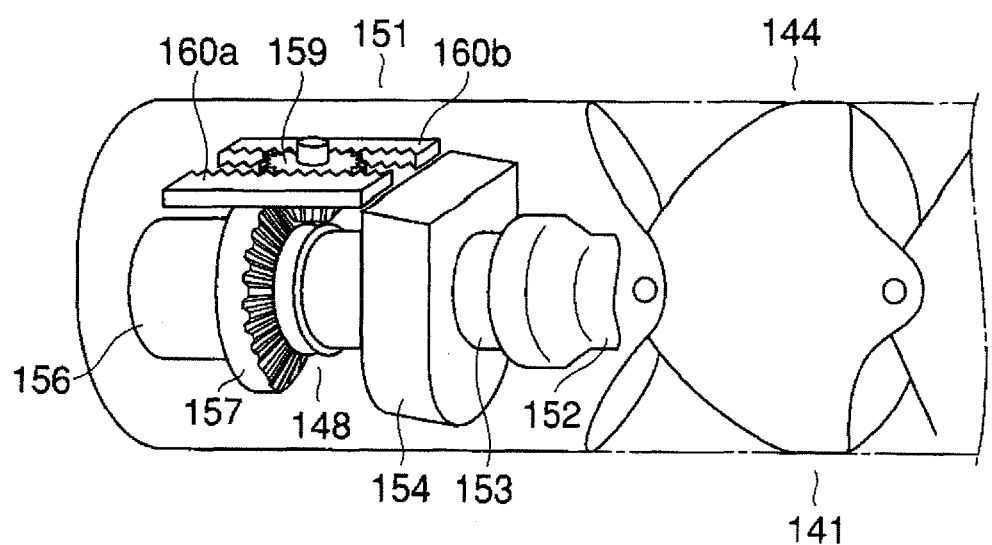
FIG. 21 is a perspective view showing a treatment tool rotating mechanism built in the distal end of the introduction guide tube in the endoscope therapeutic device according to the eighth embodiment of the present invention.

Referring now to FIG. 20 to FIG. 26, another modification of the aforementioned introduction guide tube will be described as an eighth embodiment of the present invention. As shown in FIG. 20, the introduction guide tube 140 includes a flexible insertion portion 141 and a control section 142. The control section 142 includes a grip portion 143, a plurality of angle knobs 145 for bending a bending portion 144 (see FIG. 21) of the insertion portion 141, an insertion port 147 in communication with a channel 146 (see FIG. 22) of the insertion portion 141, a treatment tool rotating knob 149a for operating a treatment tool rotating mechanism 148 described later. The angle knob 145 and the treatment tool rotating lever 149a are provided with brake knobs 145a, 149a a for locking the operating positions thereof. The control section 142 is provided with an operating button 137 for performing operations such as suction or air supply using the channel 146.

Figure 25:
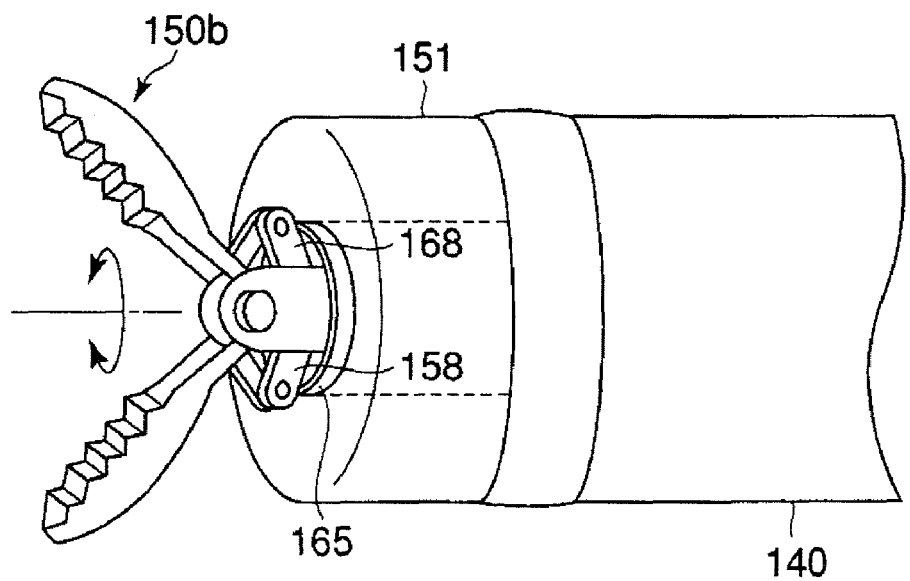
FIG. 25 is a perspective view of the distal end when the introduction guide tube of the endoscope therapeutic device according to the eighth embodiment is in use.
Figure 26:
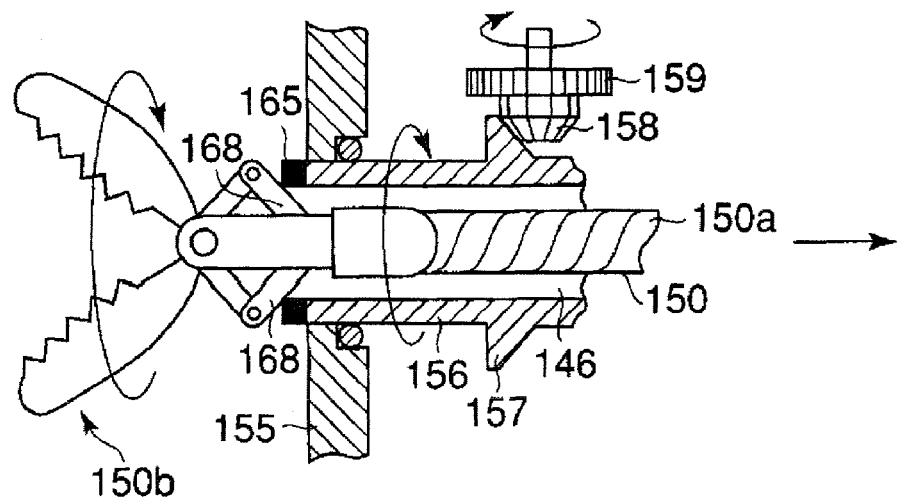
FIG. 26 is a vertical cross-sectional view of the distal end of the introduction guide tube of the endoscope therapeutic device according to the eighth embodiment when in use.

As shown in FIG. 25 and FIG. 26, by inserting an insertion portion 150a of a treatment tool 150 such as the grip forceps from the insertion port 147 of the control section 142 of the introduction guide tube 140 through the channel 146, the treatment tool 150 is projected from a distal end opening of the channel 146 into the body cavity.

Figure 22:
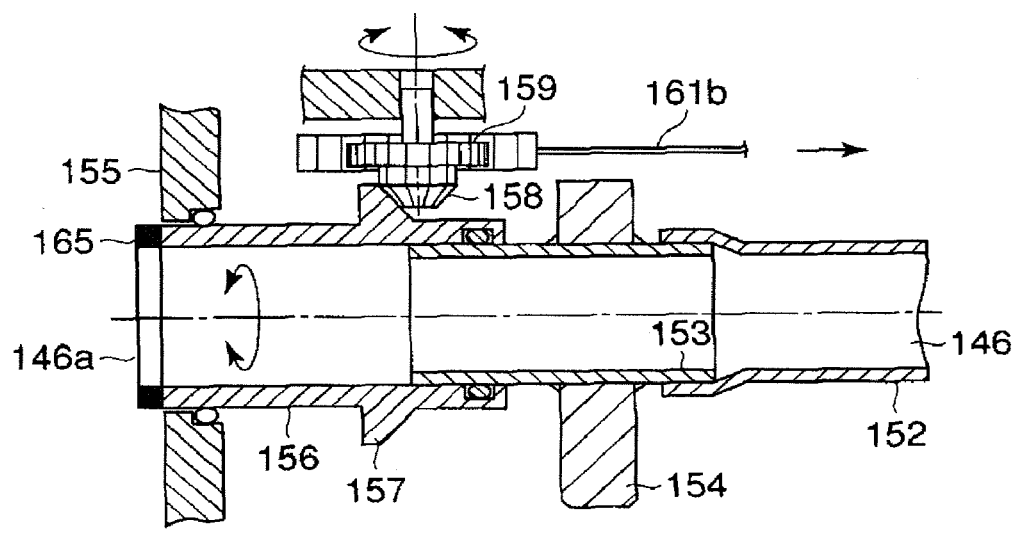
FIG. 22 is a vertical cross-sectional view of the treatment tool rotating mechanism built in the distal end of the introduction guide tube in the endoscope therapeutic device according to the eighth embodiment.

The treatment tool rotating mechanism 148 is assembled in the distal portion of the insertion portion 141, and is configured as shown in FIG. 21 to FIG. 26. In other words, a cylindrical connecting mouth ring 153, to which the distal end of a tube 152 defining the channel 146 is connected, is provided in a distal portion 151 of the insertion portion 141 of the introduction guide tube 140, and the connecting mouth ring 153 is fixed to a supporting member 154 fixed to the distal portion 151. As shown in FIG. 22, a cylindrical rotating member 156 is disposed along the connecting mouth ring 153 and a distal wall 155 of the distal portion 151, and the rotating member 156 is rotatably supported about an elongated shaft of the channel 146 or a shaft extending in parallel with the elongated shaft. The rotating member 156 opens at the distal surface of the distal portion 151 of the introduction guide tube 140 and forms a distal end opening 146a of the channel 146.

Figure 23:
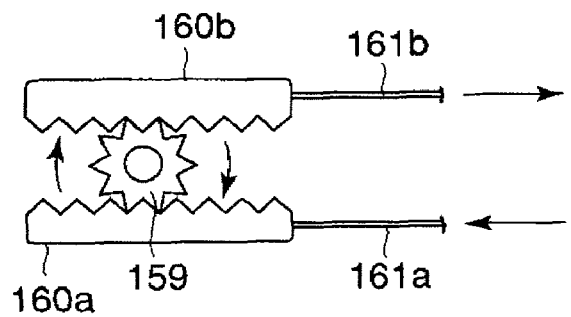
FIG. 23 is a plan view showing a gear train of the treatment tool rotating mechanism built in the distal end of the introduction guide tube in the endoscope therapeutic device according to the eighth embodiment.
Figure 24:
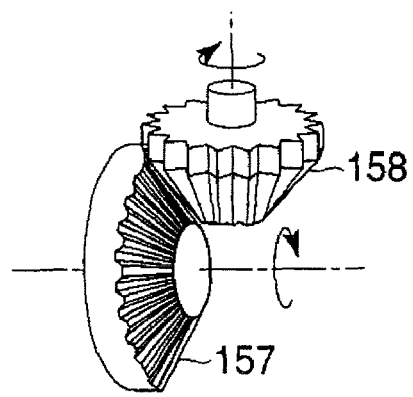
FIG. 24 is a perspective view showing the gear train of the treatment rotating mechanism built in the distal end of the introduction guide tube in the endoscope therapeutic device according to the eighth embodiment.

As shown in FIG. 22, a bevel gear 157 as a driven gear is coaxially formed on the outer periphery of the rotating member 156. A bevel gear 158 as a drive gear engages the bevel gear 157. The shaft center of the bevel gear 158 is disposed orthogonally to the shaft center of the bevel gear 157 as the driven gear. The bevel gear 158 as the drive gear is rotatably supported in the distal portion of the insertion portion 141. A pinion gear 159 is coaxially and integrally formed with the bevel gear 158. As shown in FIG. 23, a pair of racks 160a, 160b are disposed on both sides of the pinion gear 159 so as to engage therewith. The respective racks 160a, 160b are configured to be guided linearly by a guide, not shown, in the distal portion of the insertion portion 141 of the introduction guide tube 140.

Distal ends of operating wires 161a, 161b are connected to the respective racks 160a, 160b separately, and when the operator pushes or pulls the operating wires 161a, 161b from the proximal side, the racks 160a, 160b move in the fore-and-aft direction, so that the pinion gear 159 rotates.

The operating wires 161a, 161b are pulled by operating the treatment tool rotating knob 149 provided on the control section 142 to move the racks 160a, 160b.

Then, by the movement of the racks 160a, 160b, the pinion gear 159 rotates together with the bevel gear 158, and the bevel gear 158 rotates the bevel gear 157 as the driven gear. When the bevel gear 157 as the driven gear rotates, the rotating member 156 rotates together.

On the other hand, as shown in FIG. 22 and FIG. 25, a resilient member 165 formed of rubber or the like is provided at the peripheral edge of the distal end of the rotating member 156. The resilient member 165 is exposed outward from the distal portion 151 of the insertion portion 141 of the introduction guide tube 140. The resilient member 165 serves as anchoring member which abuts against the distal end of the treatment tool inserted through the channel 146, and anchors itself with respect to the distal end of the treatment tool by a frictional force against the treatment tool or deformation thereof, so as to cause the treatment tool to rotate with the rotating member 156. The treatment tool inserted through the introduction guide tube 140 can be rotated by the treatment tool rotating mechanism 148.

When the treatment tool 150 such as the grip forceps is inserted through the introduction guide tube 140 for use, as shown in FIG. 25 and FIG. 26, the operator inserts an insertion portion 150a of the treatment tool 150 through the channel 146 and allows a distal grasp member 150b of the treatment tool 150 to project from the distal end of the introduction guide tube 140.

Then, the operator opens the distal grasp member 150b by operating a link mechanism 168 for operating an openable and closable link mechanism 168, causes the distal grasp member 150b to retract slightly in the opened state, and presses the member of the link mechanism 168 against the resilient member 165 for anchoring. In other words, the distal grasp member 150b of the treatment tool 150 is joined with the rotating member 156 by a frictional force or an engaging force between the resilient member 165 and the link mechanism 168, so as to rotate with the rotating member 156.

When changing the direction of the treatment tool 150 by rotating the same, the distal grasp member 150b of the treatment tool 150 can be rotated with the rotating member 156. In other words, since the distal grasp member 150b of the treatment tool 150 is rotated directly, accurate relation with respect to the amount of rotation can be maintained, and the distal grasp member 150b of the treatment tool 150 can be rotated quickly. It is also possible to twist the elongated insertion portion 150a of the treatment tool 150 from the proximal side to assist the rotation of the distal grasp member 150b of the treatment tool 150.

Figure 27:
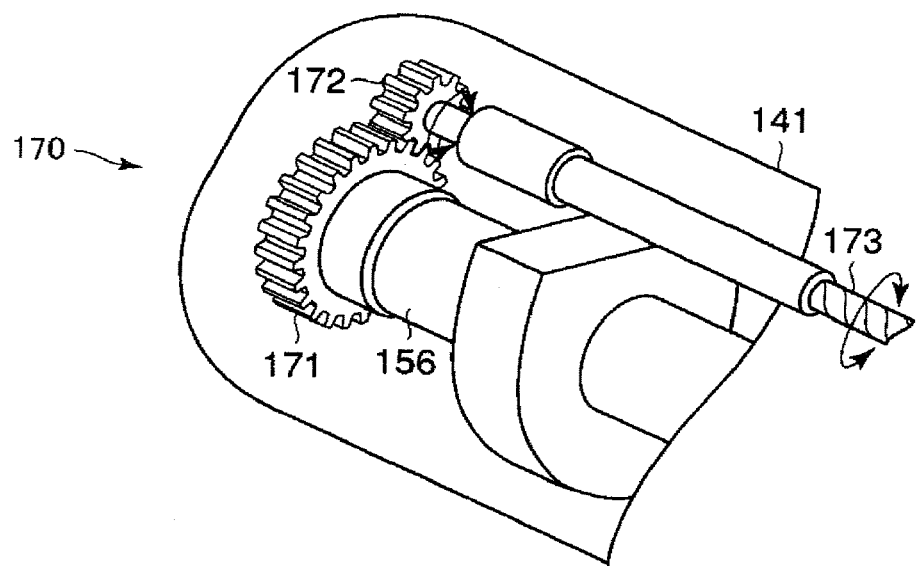
FIG. 27 is a perspective view showing the treatment tool rotating mechanism built in the distal end of the introduction guide tube in the endoscope therapeutic device according to a ninth embodiment of the present invention.
Figure 28:
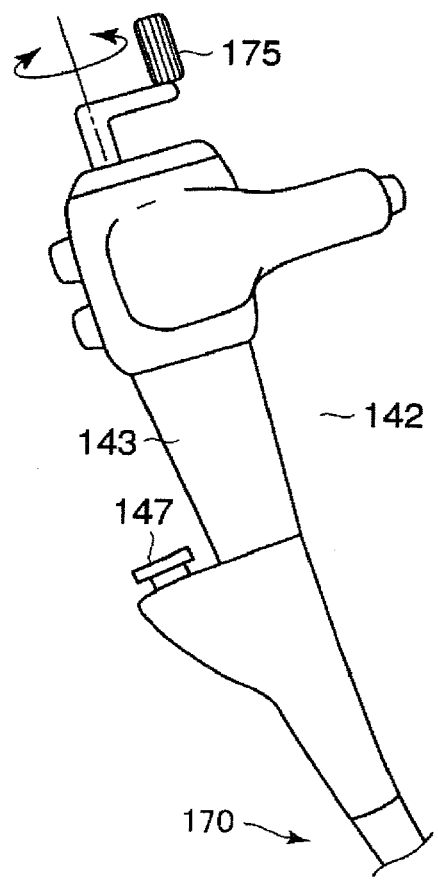
FIG. 28 is a side view of the control section of the introduction guide tube in the endoscope therapeutic device according to the ninth embodiment.

Referring now to FIG. 27 and FIG. 28, still another modification of the introduction guide tube provided with the treatment tool rotating mechanism as described above will be described as a ninth embodiment of the invention.

As shown in FIG. 27, in the treatment tool rotating mechanism of an introduction guide tube 170, the driven gear to be provided on the outer periphery of the rotating member 156 is a spur gear 171. A spur gear 172 as a drive gear engages the spur gear 171. The spur gear 172 as the drive gear is supported in the distal portion of the insertion portion 141. A distal end of a torque transmission wire 173, which is configured to transmit rotational torque, is connected to a shaft of the spur gear 172.

Then, the operator rotates the spur gear 172 as the drive gear and the spur gear 171 as the driven gear by twisting and rotating the torque transmission wire 173 from the proximal side. When the spur gear 171 rotates, the rotating member 156 rotates together therewith.

As shown in FIG. 28, a rotating lever 175 is provided on the control section 142 of the introduction guide tube 170 so that the torque transmission wire 173 is rotated by operating the rotating lever 175. The direction of operation of the operating mechanism on the proximal side by the rotating lever 175 is substantially parallel to the axis of rotation of the rotating mechanism at the distal end of the insertion portion.

The structure of the treatment tool rotating mechanism other than those described here may be substantially the same as the above-described embodiments.

In this case as well, as in the above-described embodiments, the treatment tool rotating mechanism can be used for changing the direction of rotation of the treatment tool 150. Since the driven gear is the spur gear 171 and the drive gear is the spur gear 172, and the spur gear 172 is rotated by the torque transmission wire 173, a mechanism to be built in the distal portion of the introduction guide tube 170 can be simplified.

Although the treatment tool operating mechanism for moving the treatment tool in the fore-and-aft direction or for rotating the same is such that the treatment tool is built in the distal portion of the introduction guide tube in the aforementioned description, it is also possible to combine both configurations to obtain a form in which the treatment tool operating mechanism for moving the treatment tool in the fore-and-aft direction and rotating the same.

As described above, in the introduction guide tube in a form including the treatment tool operating mechanism which moves the treatment tool in the fore-and-aft direction or/and rotating the same, the following problems can be solved.

In other words, when the direction or the position of the distal portion of the treatment tool introduced into the body cavity via the flexible introduction guide tube is changed as in the related art, the proximal portion of the treatment tool is twisted or moved in the fore-and-aft direction on the proximal side of the introduction guide tube.

However, the insertion portion of the treatment tool introduced via the interior of the introduction guide tube is elongated and flexible, and the insertion portion of the treatment tool comes into contact with the inner wall of the introduction guide tube at many points and often snakes its way therein. In particular, when the bending portion of the introduction guide tube is bent, the insertion portion of the treatment tool comes into a pressing contact with the inner wall of the introduction guide tube at the bending portion.

Under such a circumstance, even when the operator pushes and pulls the insertion portion of the treatment tool positioned in the introduction guide tube from the proximal side, or adds the rotating operation, the operating force is apt to be absorbed in route by snaking or twisting of the insertion portion of the treatment tool, and hence the operating force from the proximal side is hardly transmitted to the distal portion of the treatment tool.

However, as described above, in a form in which the operating mechanism for moving the treatment tool in the fore-and-aft direction or the operating mechanism for rotating the treatment tool is built in the distal portion of the introduction guide tube, such disadvantages can be eliminated, and quick operation is enabled while maintaining the accurate relation with respect to the operating amount. Also, a complicated operation such as to operate with an operator's hand released from the control section of the introduction guide tube or the endoscope as in a case where the operator pushes or pulls the proximal portion of the treatment tool by hand is not necessary, and hence the operation of the treatment tool in the fore-and-aft direction can be performed easily without the operator removing his/her hand from the control section.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An introduction guide tube for receiving a treatment tool used for treatment in a body cavity inserted therethrough, the introduction guide tube comprising:
   an operating mechanism provided at a distal portion of the introduction guide tube for retaining a distal end of the treatment tool inserted through the introduction guide tube and for moving the distal end of the treatment tool,
   a wire being inserted through the introduction guide tube and being capable of freely moving forward or backward along an axis direction of the introduction guide tube, wherein
   the operating mechanism comprises a rotating mechanism, the rotating mechanism is configured to convert a linear motion into a rotary motion, wherein in the linear motion, the wire moves along the axis direction of the introduction guide, and in the rotary motion, the treatment tool rotates around an axis of rotation corresponding to a longitudinal axis of a treatment tool insertion channel of the introduction guide tube or to an axis extending in parallel with the longitudinal axis.

2. An introduction guide tube according to claim 1, wherein the operating mechanism comprises an engaging member that engages part of an insertion portion of the treatment tool.

3. An introduction guide tube according to claim 2, further comprising a mechanism for selectively engaging and disengaging the engaging member, the mechanism being actuated from a proximal side of the introduction guide tube.

4. An introduction guide tube according to claim 1, wherein the operating mechanism comprises a moving mechanism for moving the distal end of the treatment tool in a fore-and-aft direction along a longitudinal axis of a treatment tool insertion channel of the introduction guide tube or an axis extending in parallel with the longitudinal axis.

5. An insertion guide tube according to claim 1, wherein the rotating mechanism rotates in a same direction as an operating direction of the operating mechanism from the proximal side of the introduction guide tube.

6. An introduction guide tube for receiving a treatment tool used for treatment in a body cavity inserted therethrough, the introduction guide tube comprising:
   an operating mechanism provided at a distal portion of the introduction guide tube for retaining a distal end of the treatment tool inserted through the introduction guide tube and for moving the distal end of the treatment tool,
   a wire being inserted through the introduction guide tube and being capable of freely moving forward or backward along an axis direction of the introduction guide tube, wherein the operating mechanism is a rotating mechanism for rotating the distal end of the treatment tool, the rotating mechanism is configured to convert a linear motion into a rotary motion, wherein in the linear motion, the wire moves along the axis direction of the introduction guide, and in the rotary motion, the treatment tool rotates around an axis of rotation corresponding to a longitudinal axis of a treatment tool insertion channel of the introduction guide tube or to an axis extending in parallel with the longitudinal axis.

* * * * *